US00PP26713P3

(12) United States Plant Patent
Miller

(10) Patent No.: US PP26,713 P3
(45) Date of Patent: May 10, 2016

(54) ***PITTOSPORUM* PLANT NAMED 'SEASIDE'**

(50) Latin Name: *Pittosporum tenuifolium*
Varietal Denomination: SEASIDE

(71) Applicant: Luen Miller, Santa Cruz, CA (US)

(72) Inventor: Luen Miller, Santa Cruz, CA (US)

( * ) Notice: Subject to any disclaimer, the term of this patent is extended or adjusted under 35 U.S.C. 154(b) by 228 days.

(21) Appl. No.: 13/999,018

(22) Filed: Dec. 31, 2013

(65) Prior Publication Data

US 2015/0189809 P1 Jul. 2, 2015

(51) Int. Cl.
*A01H 5/00* (2006.01)

(52) U.S. Cl.
USPC ..... Plt./234

(58) Field of Classification Search
USPC ..... Plt./226, 234
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Pittosporum* cultivar named 'SEASIDE' is disclosed, characterized by typically undulating, oblong leaves and dense growth habit. Branches of the plant arise at an acute angle. The new variety is a *Pittosporum*, typically produced as an outdoor ornamental plant.

2 Drawing Sheets

Figure 1:
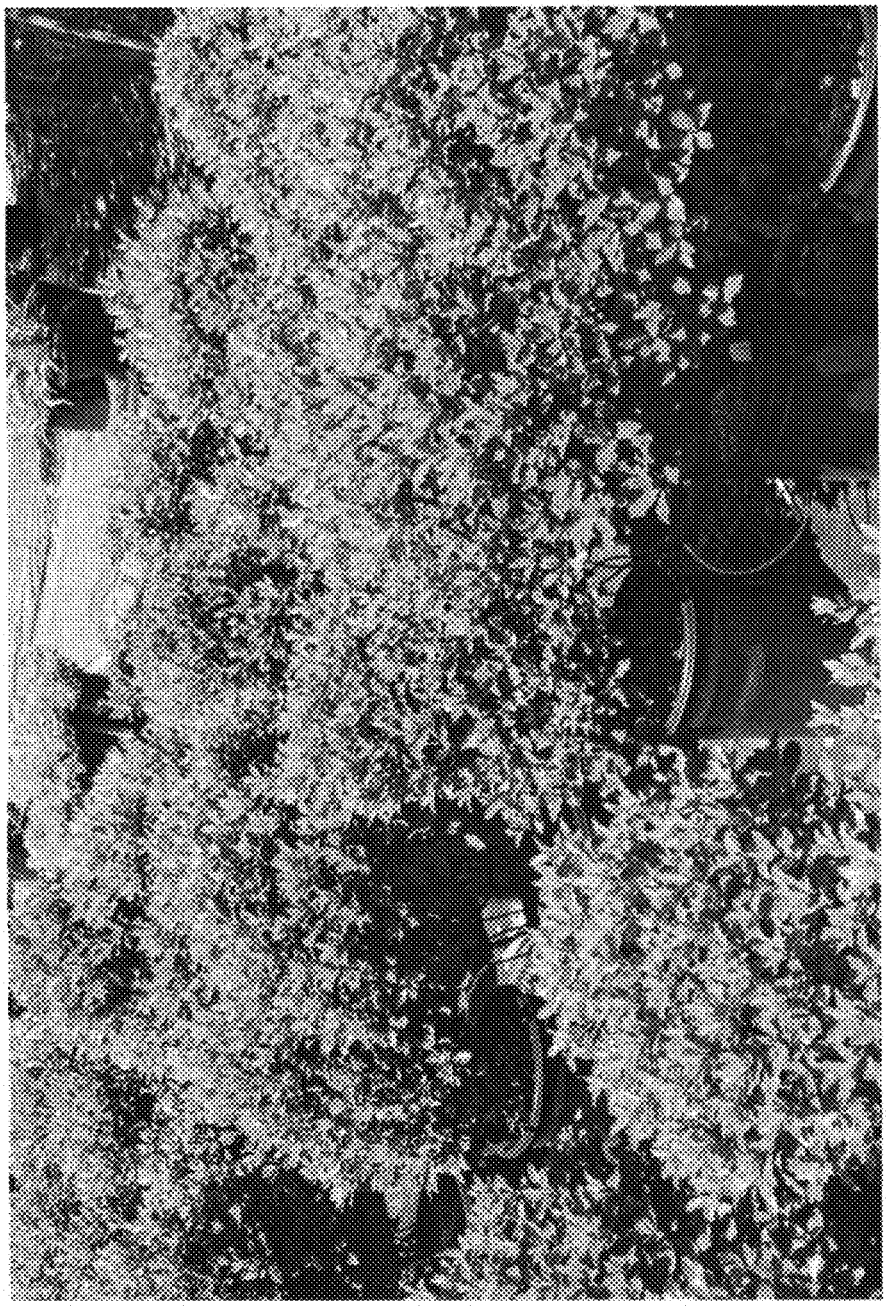

Latin name of the genus and species: *Pittosporum tenuifolium.*

Variety denomination: 'SEASIDE'.

BACKGROUND OF THE INVENTION

The new cultivar is the product of a controlled breeding program. The new variety was discovered as a seedling from a group of 6 seeds collected from the parent variety, *Pittosporum tenuifolium* 'Golf Ball', U.S. Plant Pat. No. 15,329. The pollen parent is unknown, several *Pittosporum* varieties were present in the commercial field. After several season of observation, and confidential testing, 'Seaside' was selected as a superior cultivar in May of 2010, by the inventor, Luen Miller at a commercial nursery in Royal Oaks, Calif.

Asexual reproduction of the new cultivar 'SEASIDE' was first performed by vegetative cuttings in September of 2011 at a commercial nursery in Royal Oaks, Calif. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'SEASIDE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SEASIDE.' These characteristics in combination distinguish 'SEASIDE' as a new and distinct *Pittosporum* cultivar:

1. Dense growth.
2. Typically undulating leaves.
3. Oblong foliage shape.
4. Acute angle of attachment of lateral branches.

PARENT COMPARISON

Plants of the new cultivar 'SEASIDE' are similar to the parent, *Pittosporum* 'Golf Ball' in most horticultural characteristics. 'SEASIDE' however, differs in producing longer, narrower foliage, with an undulating aspect not found in foliage of 'Golf Ball'. Additionally, plants of 'SEASIDE' are denser than plants of 'Golf Ball'. The angle of branches of 'SEASIDE' is significantly more acute than the angle of branches of 'Golf Ball'.

COMMERCIAL COMPARISON

Plants of the new cultivar 'SEASIDE' can be compared to the commercial variety 'Elfin' U.S. Plant Pat. No. 21,822. Plants of the these cultivars are similar in most horticultural characteristics, however, 'SEASIDE' differs in producing longer, narrower foliage with an undulating aspect not found in foliage of 'Elfin'. Additionally, plants of 'SEASIDE' are larger and denser than plants of 'Elfin'. The angle of branches of 'SEASIDE' is significantly more acute than the angle of branches of 'Elfin'.

Plants of the new cultivar 'SEASIDE' can be compared to the commercial variety 'Silver Ball' U.S. Plant Pat. No. 25,705. Plants of the these cultivars are similar in most horticultural characteristics, however, 'SEASIDE' differs in the following:

1. Foliage of 'Seaside' is Green, whereas foliage of 'Silver Ball' is Grey-Green with an irregular white margin.
2. Foliage of 'Seaside' has a strong undulation not found in foliage of 'Silver Ball'.

BRIEF DESCRIPTION OF THE PHOTOGRAPHS

The accompanying photograph in FIG. 1 illustrates in full color a typical plants of 'SEASIDE' grown in Royal Oaks, Calif. Plants are approximately 2 years old.

Figure 2:
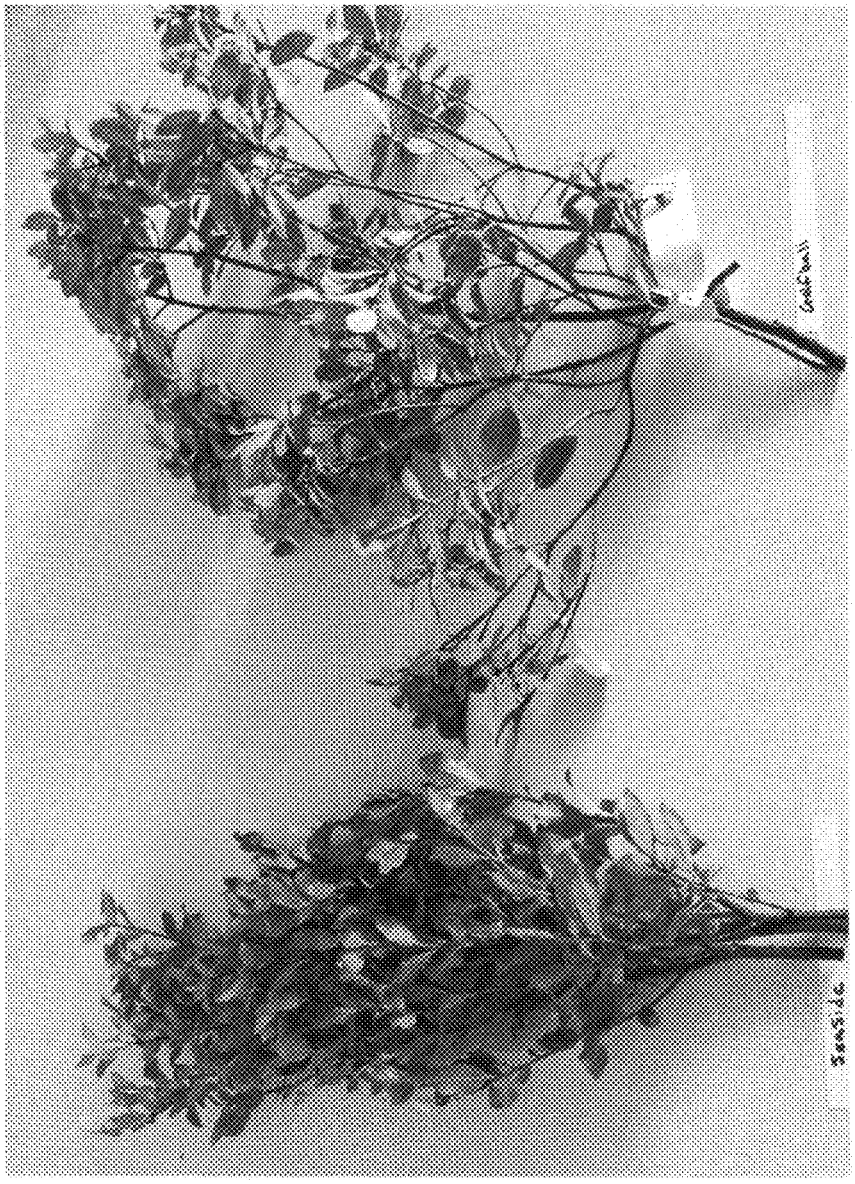

FIG. 2 illustrates in full color branches of 'SEASIDE' compared with branches of 'Golf Ball'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SEASIDE' plants grown outdoors in Royal Oaks, Calif. Plants are approximately 1 year old. Temperatures ranged from approximately 1° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Pittosporum tenuifolium* 'SEASIDE'.

PROPAGATION

Root description: Fine root system colored near Brown 199D and N199B.

PLANT

Growth habit: Roughly ovate, dense woody evergreen shrub.
Height: Approximately 45 cm for a one year old plant.
Plant spread: Approximately 40 cm.
Growth rate: Moderate to rapid.
Diameter of stem: Approximately 0.35 cm.
Color of stem: Mature stems near RHS Brown N200B. Young growth near Brown N200A.
Texture of stem: Minutely and irregularly ridged.
Angle of stem: Lateral stems are straight and attached at acute angles between 10 to 45 degrees from the main stems.
Internode length: Between 0.5 cm and 1.5 cm.

FOLIAGE

Leaf:

*Arrangement*.—Alternate.
*Quantity*.—Approximately 14 per lateral branch.
*Average leaf length*.—Approximately 2.9 cm, including petiole.
*Average leaf width*.—Approximately 1.2 cm.
*Shape of blade*.—Oblong.
*Apex*.—Acute.
*Base*.—Rounded.
*Margin*.—Shallow serrate.
*Texture of top surface*.—Glabrous.
*Texture of bottom surface*.—Glabrous.
*Appearance upper surface*.—Matte.
*Appearance lower surface*.—Matte.
*Aspect*.—Undulating and somewhat downwardly cupped.
*Color*.—Young foliage upper side: Near RHS Yellow-Green 144A. Young foliage under side: Near RHS Green 138B. Mature foliage upper side: Near RHS Green 137B. Mature foliage under side: Near RHS Yellow-Green 146A.
*Venation*.—Type: Pinnate. Venation color upper side: Near RHS Yellow-Green 145B. Venation color under side: Near RHS Yellow-Green 145C.
*Petiole*.—Length: Average 0.5 cm. Diameter: Approximately 0.1 cm. Color: Near RHS Brown 200B. Texture: Glabrous.

FLOWER

Not observed to date.

OTHER CHARACTERISTICS

Fruit and seed: None observed to date.
Disease resistance: Neither resistance nor susceptibility to normal diseases and pests of *Pittosporum* observed.
Temperature tolerance: Not tested but expected to handle some frost, and high temperatures without humidity. Expected range from approximately −5° C. to 40° C.
Drought tolerance: Will tolerate some dryness once established.

What is claimed is:

1. A new and distinct cultivar of *Pittosporum* plant named 'SEASIDE' as herein illustrated and described.

* * * * *